United States Patent [19]

Lindstrom et al.

[11] Patent Number: 4,886,786

[45] Date of Patent: Dec. 12, 1989

[54] ADDITIVE FOR IRRIGATION SOLUTION OR SURGICAL SOLUTION

[76] Inventors: Richard L. Lindstrom, 20050 Lakeview Ave., Excelsior, Minn. 55331; Debra L. Skelnik, P.O. Box 344, Rt. 5, Cambridge, Minn. 55008

[21] Appl. No.: 151,480

[22] Filed: Feb. 2, 1988

Related U.S. Application Data

[63] Continuation-in-part of Ser. No. 761,407, Aug. 1, 1985, Pat. No. 4,696,917, which is a continuation-in-part of Ser. No. 836,156, Mar. 4, 1986, Pat. No. 4,725,586.

[51] Int. Cl.$^4$ ............................................. A61K 31/70
[52] U.S. Cl. ....................................... 514/54; 514/23; 514/21; 514/2
[58] Field of Search ......................... 514/54, 23, 21, 2

[56] References Cited

U.S. PATENT DOCUMENTS 4,024,237  5/1977  Eichel et al. ........................... 514/54
4,725,586  2/1988  Lindstrom et al. ................... 514/59

Primary Examiner—Johnnie R. Brown
Assistant Examiner—Elli Peselev
Attorney, Agent, or Firm—Hugh D. Jaeger

[57] ABSTRACT

An additive for intraocular irrigation solution or surgical solution which provides the anterior chamber and posterior chamber of the eye with protection during surgical procedures that require irrigation. The additive for the solutions is composed of a balanced salt solution containing dextrose supplemented with chondroitin sulfate. Other chemical compositions can supplement the additive.

6 Claims, No Drawings

ADDITIVE FOR IRRIGATION SOLUTION OR SURGICAL SOLUTION

CROSS REFERENCES TO CO-PENDING APPLICATIONS

This application is a continuation-in-part of Ser. No. 761,407, filed Aug. 1, 1985, entitled Irrigation Solution, now U.S. Pat. No. 4,696,917, which is a continuation-in-part of Ser. No. 836,156, filed Mar. 4, 1986, entitled Surgical Solution, now U.S. Pat. No. 4,725,586.

BACKGROUND OF THE INVENTION

1. Field of the Invention

The present invention pertains to an additive for an irrigation solution or a surgical solution for the anterior and posterior chamber of the eye. The additive can also be used in other solutions, such as corneal preservation medium, for other surgical or medical applications.

2. Description of the Prior Art

There are two intraocular irrigation solutions commonly being used in ophthalmic surgeries. These two irrigation solutions are balanced salt solution and BSS Plus. BSS is a balanced salt solution that incorporates a sodium citrate and sodium acetate buffering system. BSS Plus consists of a balanced salt solution with a bicarbonate buffering system, with glucose added as an additional osmotic agent and energy source. An additional component, oxidized glutathione, is reduced by the ocular cells and serves as an anti-oxidant. In addition, Lactated Ringers Solution is used when BSS and BSS Plus are not available.

SUMMARY OF THE INVENTION

The general purpose of the present invention is an additive for an irrigation solution or surgical solution which provides the anterior and posterior chamber of the eye protection during surgical procedures that require irrigation. This additive specifically protects the corneal endothelium in anterior segment surgery. The corneal endothelium and other anterior and posterior chamber structures are in direct contact with the additive in the solution.

According to one embodiment of the present invention, an additive includes: 1. A protective coating agent of a highly negatively charged glycosaminoglycan such as chondroitin sulfate which is a naturally occurring, biodegradable material normally found in the human cornea; In some cases, 2. An effective antioxidant such as 2-mercaptoethanol, that can be utilized in both the oxidized and reduced forms by human corneal endothelial cells. 2-mercaptoethanol is used as a carrier of cystine into the cells. Cystine may well be the limiting amino acid for the synthesis of protein as well a glutathione. The addition of 2-mercaptoethanol increases the intracellular level of glutathione, and aids in membrane and maintenance of cell junctional complexes; 3. An energy source, such as dextrose, is the starting molecule for glycolysis, a central pathway for recovery of chemical energy as ATP (adenosine triphosphate). 4. An additional energy source such as a pyruvate, is provided for additional biosynthetic synthesis that may be required by the ocular cells after surgical trauma. 5. An amino acid cystine in the presence of 2-mercaptoethanol, is provided so that corneal endothelial cells can constantly utilize cystine in the additive, and maintain intracellular cystine and glutathione levels during intraocular perfusion. 6. A bicarbonate buffer system, important in intracellular fluid, helps maintain intercellular pH, fluid movement, corneal deturgesence, and membrane potential difference across the corneal endothelium.

The base medium of the irrigation solution or surgical solution with the additive consists of a Balanced Salt Solution or Lactated Ringers Solution containing five essential ions.

One significant aspect and feature of the additive of the present invention is to protect the anterior and posterior segments of the cornea during surgical procedures, to maintain homeostasis after surgical trauma, and to provide necessary metabolic substrates that may be needed for wound repair.

Another significant aspect and feature of this additive is use in other applications when added to the irrigation solution, such as: 1. An ophthalmic irrigating and lubricating eye drop; 2. In the solution for burn wounds; 3. As a general surgical solution for use in surgeries where a solution is required; 4. As a vehicle for ophthalmological drugs, such as drops; 5. As an anticataract drug; 6. As an eye drop; 7. As a corneal preservation medium additive; 8. As a general irrigation solution including orthopedics, such as athroscopy; urology, such as cystoscopy; neurosurgery; as well as in artificial insemination, obstetrics, and gynecology (OBGYN); 9. As a woundhealing solution; or 10. As an anti-ulcer drug.

DESCRIPTION OF THE PREFERRED EMBODIMENTS

The solution additive such as to an irrigation solution or a surgical solution is used at a concentration of 1–100 parts for each 500 parts of a commercially available balanced salt solution (BSS) base such as that sold by Iolab or Alcon.

Typically, the additive concentrate contains one or more of the components in Table A.

TABLE A

| Component | Range | Preferred Component |
| --- | --- | --- |
| glycosaminoglycan | 0.001–550 mg/ml | chondroitin sulfate |
| an antioxidant | 0–10 mM | 2-mercaptoethanol |
| energy source | 0–20 mM | dextrose |
|  | 0–20 mM | pyruvate |
| amino acid | 0–10 mM | cystine |
| buffer | 0–100 mM | sodium bicarbonate |

The formulation is a representative concentration of the additive made up in a total volume of 1–50 ml balanced salt solution or water.

The additive can then be added to 500 ml of balanced salt solution as in Table B. This irrigation solution additive is therefore defined at proportionate concentrations at all other volumes

TABLE B

| Additive of 50 ml made up in | |
| --- | --- |
| Balance Salt Solution (BSS) Base Medium: | |
| chondroitin sulfate | 44.00 mg/ml |
| 2-mercaptoethanol | 5.50 mM |
| dextrose | 55.0 mM |
| pyruvate | 11.00 mM |
| cystine | 33.00 mM |
| sodium bicarbonate | 275.00 mM |
| Balance Salt Solution (BSS) Base Medium: | |
| sodium chloride | .64% |
| potassium chloride | .075% |
| calcium chloride | .048% |
| magnesium chloride | .030% |
| sodium acetate | .39% |

TABLE B-continued

| Additive of 50 ml made up in | |
|---|---|
| sodium citrate | .17% |

Or made up in distilled injection grade water. The final concentration of the additive after dilution with an appropriate amount of Balance Salt Solution is described in Table C.

TABLE C

| | Final Concentration | |
|---|---|---|
| Component | Final Concentration | Approximate Ranges of final concentration |
| chondroitin sulfate | 4.00 mg/ml | (0-100 mg/ml) |
| 2-mercaptoethanol | 0.50 mM | (0-2 mM) |
| dextrose | 0.92 mg/ml | (0-20 mM) |
| pyruvate | 1.00 mM | (0-20 mM) |
| cystine | 1.00 mM | (0-10 mM) |
| sodium bicarbonate | 25.00 mM | (0-100 mM) |

This additive is therefore defined at proportionate concentrations at all other volumes.

GROUPINGS

An additive concentrate comprising one or more of the following components in Balanced Salt or like solution. (lyophilized)
a. a glycosaminoglycan: 1.0 mg/ml to 550 mg/ml.
  1. chondroitin sulfate
  2. dermatan sulfate
  3. heparan sulfate
  4. heparin sulfate
  5. keratan sulfate
  6. hyaluronic acid
b. an antioxidant
  1. ascorbic acid: 1 mM-20 mM
  2. glutathione in: 10 µg/ml 14 500 mg/ml
  3. Dl-γ-tocopheral: 0.01 mg/ml-1 mg/ml
  4. 2-mercaptoethanol: 0.1 mM to 8 mM
c. Glycoproteins that promote cellular adhesion and migration:
  1. Laminin, a large glycoprotein having a molecular weight of approximately 1,000,000 daltons. The laminin molecule has the shape of an asymmetric cross, comprised of 3 B chains of 200,000 daltons each, and one A chain of 400,000 daltons. The chains are held together by disulfide bonds. The single A chain contains a binding site for heparin sulfate. The B chains contain type IV collagen binding sites. The intersection of the three B chains is the locus for cell binding. Laminin provides cells with physiological compatible extracellular matrix that will foster attachment cytoplasmic spreading and proliferation.
  Laminin: 1 µg/ml-300 mg/ml
  2. Fibronectin is an extracellular matrix-associated glycoprotein composed of two disulfide bonded subunits of 220,000 daltons each. Fibronectin has the potential to interact with several cell surface associated macromulecules including collagen, glycosaminoglycans and cell surface receptors. Fibronectin promotes cell adhesion and migration of human corneal endothelial cells, epithelial cells and fibroblasts.
  Fibronectin: 100 ng/ml-100 mg/ml
d. Cell growth factors or growth supplements:

1. Fibroblastic growth factor (FGF), a single chain polypeptide, isolated and purified from the pituitary, human (hFGF) fibronectin or bovine fibronectin (bFGF), acidic or basic forms. Molecular weight range of 14K to 16K. This factor has been demonstrated mitogenic in vitro to a wide variety of cells comprising mesoderm and neuroectoderm tissue.
  This also includes synthetic formulated FGF basic peptides consisting of: (1-24)

Pro—Ala—Leu—Pro—Glu—Asp—Gly—Gly—Ser—Gly—
  Ala—Phe—Pro—Pro—Gly—His—Phe—Lys—Asp—Pro—
  Lys—Arg—Leu—Try and synthetic formulated FGF acidic peptides consisting of: (1-11)
  Phen-Asn-Leu-Pro-Leu-Gly-Asn-Tyr-Lys-Lys-Pro
  Fibroblastic growth factor: 100 ng/ml-100 mg/ml 2. Endothelial cell growth supplement (ECGS), prepared from the hypothalamus as a lyophilized extract. This growth supplement has demonstrated mitogenic in vitro to a wide variety of endothelial cells; i.e., human corneal endothelial cells, human umbilical vein endothelial cells, and mouse Balb/c fibroblasts.
  Endothelial Cell Growth supplement: 200 µg/ml-500 mg/ml 3. Urogastrone or Epidermal growth factor (EGF), a single chained polypeptide, is composed of 53 amino acids, containing 3 disulfide bonds and has been isolated from mouse submaxillary glands (mEGF) and human urine (hEGF). This growth factor has been demonstrated to be mitogenic in vitro for a wide variety of cells of ectodermal and mesodermal origin.
  This also consists of synthetic mouse EGF:

Asn—Ser—Tyr—Pro—Gly—Cys—Pro—Ser—
  Ser—Tyr—Asp—Gly—Tyr—Cys—Leu—Asn—
  Gly—Gly—Val—Cys—Met—His—Ile—Glu—
  Ser—Leu—Asp—Ser—Tyr—Thr—Cys—
  Asn—Cys—Val—Ile—Gly—Tyr—Ser—Gly—
  Asp—Arg—Cys—Gln—Thr—Arg—Asp—
  Leu—Arg—Trp—Trp—Glu—Leu—Arg
  And synthetic EGF [Cys(Acm) 20'31] (20-31)
  Cys—(Acm)—Met—His—Ile—Glu—Ser—Leu—Asp—
  Ser—Tyr—Thr—Cys(Acm)
  And human EGF synthetic receptor peptide:
  Asp—Val—Val—Asp—Ala—Asp—Glu—Tyr—Leu—Ile—
  Pro—Gln Epidermal Growth Factor: 0.1 µg/ml-100 mg/ml
  4. Bovine pituitary extract (BPE) an aqueous extract of bovine or human pituitary glands. This growth supplement has demonstrated mitogenic in vitro to a wide variety of epithelial cells; i.e., human corneal epithelium, human epidermal keratinocytes
  Bovine Pituitary Extract: 100 ng-500 mg/ml
  5. Insulin a polypeptide hormone that functions in the regulation of cellular carbohydrate metabolism and the synthesis of cellular protein, RNA and neutral lipids.
  Insulin: 0.1 ug/ml-10 mg/ml
  6. Transferrin: 0.1 µg/ml-10 mg/ml
  7. Sodium Selenite: 0.1 ng/ml-100 µg/ml
e. Extracellular Matrix Proteins 1. IV collagen: the main collagen in basal laminae. IV collagen in a range of about 5 mg/ml-10 g/ml.
2. Enactin in a range of about 1 μg/ml-100 mg/ml.

f. Buffering Agents:
   1. HEPES buffer (N'-2-hydroxyethylpiperazine-N'-Ethanesulfonic Acid)
      HEPES buffer: 10 mM-250 mM
   2. Sodium bicarbonate: 0.01 mM to 250 mM g. Energy Sources:
   Pyruvate: 5 mM-100 mM
   2. dextrose: 0.5 mM-100 mM h. Amino Acids: 0.01 mM-50 mM
   1. Cystine
   2. Inosine
   3. Adenine
   4. Adenosine i. Precursors of cell membrane lipids:
   ethanolamine: 0.01 mM-20 mM
   2. phosphoethanolamine: 0.01 mM-20 mM
   3. sialic acid: 0.001 mM-10 mM

EFFECT OF TWO HOUR IRRIGATION WITH BALANCED SALT SOLUTION WITH ADDITIVE WITHOUT CYSTINE ON THE GLUTATHIONE CONTENT OF CAT LENSES

To determine that the in vitro effects of 2-mercaptoethanol could be duplicated in vivo, the following studies were done. In two hour anterior chamber perfusion studies, using a balanced salt solution with additive (chondroitin sulfate 4.0 mg/ml; 2-mercaptoethanol 0.5 mM; dextrose 0.92 mg/ml; pyruvate 1.0 mM; sodium bicarbonate 25 mM) (without cystine) in cats, the glutathione content of the lens was compared to the non-irrigated control 24 hours after perfusion.

|  | Irrigation with Additive | Control |
| --- | --- | --- |
| Total Glutathione | 1530.27 ± 26.03 ug/lens | 1435.39 ± 46.39 ug/lens |
| 6.20% Difference | | |

A 6.2% difference in total glutathione was seen between the irrigated lens and the control lens. This increase in glutathione content is due to de novo synthesis.

EFFECT OF TWO HOUR IRRIGATION WITH BALANCED SALT SOLUTION WITH ADDITIVE CONTAINING 3 mM CYSTINE ON THE GLUTATHIONE CONTENT OF CAT LENSES

To determine if the in vivo effect of the irrigation additive, containing 2-mercaptoethanol, could be enhanced by the addition of 3 mM cystine, the following studies were done. In two hour anterior chamber perfusion studies, using a balanced salt solution with the additive containing 3 mM cystine, in cats, the glutathione content of the perfused lens was compared to the non-irrigated control 24 hours after perfusion.

| BSS with Additive with 3 mM Cystine | Control |
| --- | --- |
| Total Glutathione  1495.73 ± 35.75 ug/lens | 1378.25 ± 31.25 ug/lens |
| 7.85% Difference | |

A 7.85% increase in total glutathione was seen between the irrigated lens and the control lens. This increase in glutathione content is due to de novo synthesis. Balanced salt solution with additive containing 3 mM cystine appears to have enhanced the effect of 2-mercaptoethanol, in vivo by increasing the lens concentration of glutathione.

THE EFFECT OF 2-MERCAPTOETHANOL ON HUMAN AND RABBIT LENS IN VITRO

In the investigational work with human corneal endothelial cells, it is recognized the limited capacity to synthesize cystine via the methionine pathway. In addition, corneal endothelial cells are deficient in capacity to uptake cystine, and that intracellular cystine and glutathione contents decrease considerably in normal culture medium containing cystine. Then examined was the glutathione content of human and rabbit lenses. Reduction of glutathione content in human lens has been associated with the formation of certain types of cataracts. Glutathione is made up of three amino acids, cystine, glutamic acid, and glycine. Cystine has been implicated as the limiting amino acid for the synthesis of protein as well as glutathione. An increase in the intracellular cystine pool by the addition of 2-mercaptoethanol may cause the increase in cellular glutathione content, because the cellular pool of cystine is very low as compared with that of glutamic acid and glycine.

In three days, in vitro rabbit lens incubation studies utilizing 2-mercaptoethanol, the glutathione content of the lens was compared to the control lens incubated without mercaptoethanol.

|  | Medium with 2-mercaptoethanol | Control |
| --- | --- | --- |
| Total Glutathione | 657.61 ± 24.70 ug/lens | 615.5 ± 24.70 ug/lens |
| Percent Oxidized | 3.94 | 8.54 |
| 6.4% Difference in Total Glutathione | | |

Only a small difference in total glutathione was found in these studies. The rabbit lens is capable of producing enough cystine to maintain intracellular glutathione levels during lens incubation in vitro. The 2-mercaptoethanol was able to maintain the glutathione in a reduced form greater than the control.

In three day, in vitro human lens incubation studies utilizing 2-mercaptoethanol, the glutathione content of the lens was compared to the control lens incubated without 2-mercaptoethanol.

|  | Medium with 2-mercaptoethanol | Control |
| --- | --- | --- |
| Total Glutathione | 230.91 ± 15.49 ug/lens | 176.16 ± 2.26 ug/lens |
| Percent Oxidized | 13.02 | 17.87 |
| 23.70% Difference in Total Glutathione | | |

With the media containing 2-mercaptoethanol, there was a 23.7% increase in the total glutathione content mainly in the reduced form.

MODE OF OPERATION

The base of this additive is a completely defined balance salt solution supplemented with dextrose and with the addition of one to five corneal and retinal enhancing agents. These are chondroitin sulfate, 2-mercaptoethanol, pyruvate, cystine, and sodium bicarbonate. The exposure time to the additive solution in the normal ophthalmic surgical procedure, such as an intraocular lens implant, is normally 3-8 minutes, a very limited time period. But upon special occasions, the anterior chamber is filled with the solution and allowed to remain there until the aqueous humor is remade, which may take up to 24 hours. During this time the anterior chamber cells are deprived of necessary nutrients, normally supplied by the aqueous humor. Although the anterior segment cells, most significantly the corneal endothelium, are supplied with nutrients from their basal side, most of the metabolic uptake is from the anterior surface. The corneal endothelium maintains the clarity of the cornea by actively pumping salts and water out of the connective tissue stroma into the anterior chamber of the eye. The $Na^+/K^+$ ATPase pump of these endothelial cells requires ATP and reduced pump sites to keep this pump working. When the pumping action of these corneal endothelial cells is reduced, the cornea imbibes fluids and becomes thickened and loses optical clarity.

Therefore, an irrigation solution with an additive with a reducing agent is of considerable advantage. One of the major disadvantages of BSS Plus, with the reducing agent glutathione and the bicarbonate buffering system, is the lack of stability of the solution once prepared. The glutathione component of the solution is added separately, and the solution is stable for only a 24 hour period. The buffering ability of the bicarbonate in BSS Plus is greatly reduced once the solution is exposed to the atmosphere.

The present additive provides the reducing agent 2-mercaptoethanol, that can be utilized in both the reduced and oxidized forms eliminating the instability of a glutathione containing irrigation solution. This effective reducing agent can be utilized by human corneal endothelial cells.

Five additional components have been added to the solution to increase its effectiveness in protecting and repairing the anterior segment of the cornea during and after surgical trauma. (1) Chondroitin sulfate, a highly negative charged glycosaminoglycan is added to replace any glycosaminoglycans that may be removed from the surface of the corneal endothelial cells from the disruption of aqueous flow or surgical trauma. Glycosamimoglycans are necessary for membrane stability and the maintenance of the three-dimensional structure of receptor proteins. These receptor proteins are required for the metabolic processes of the cell. Chondroitin sulfate acts as a protective coating for the anterior segment cells.

An additional substrate, (2) pyruvate, is provided for additional biosynthetic synthesis that may be required by these anterior segment cells after surgical trauma. There are 20 standard amino acids in proteins, all having different carbon skeletons. Correspondingly, there are 20 different catabolic pathways for their degradation. Carbon skeletons of 10 of the amino acids are ultimately broken down to yield acetyl-CoA which enters the citric acid cycle directly. Five of the ten are degraded to acetyl-CoA via pyruvate. The five amino acids entering via pyruvate are alanine, cystine, glycine, serine, and threonine.

(3) 2-mercaptoethanol, an anti-oxidant, used in the proposed irrigation additive has been shown to be effective at concentrations of 10 to 1000 $\mu M$, and its action resembles those of macrophages or feeder layer cells. It is proposed that human corneal endothelial cells have a low capacity to synthesize cystine via the methionine pathway. Methionine furnishes the sulfur atom and serine furnishes the carbon chain in the biosynthesis of cystine. The end result of a complex series of reactions is the replacement of the —OH group of serine with an —SH group, derived from methionine, to form cystine.

In addition, corneal endothelial cells are deficient in their capacity to take up cystine and that intracellular cystine and glutathione contents decrease considerably in normal culture medium containing cystine. In the presence of 2-mercaptoethanol, corneal endothelial cells constantly utilize (4) cystine in the irrigation solution and the cellular cystine and glutathione levels are maintained during intraocular perfusion. This effect seems to be the most crucial function of 2-mercaptoethanol in stimulating the growth of the cells and is not explained by mere reduction of cystine to cystine in the irrigation solution. It is the mixed disulfide of 2-mercaptoethanol and cystine, which is formed by the reaction of 2-mercaptoethanol with cystine in the irrigation solution, that plays an important role in the action of 2-mercaptoethanol.

The 2-mercaptoethanol acts repeatedly as a carrier of cystine. The 2-mercaptoethanol does not accumulate in the cells, and it escapes to the irrigation solution and reacts with the cystine. Thus, 2-mercaptoethanol is continuously taken up by the cells in the form of the mixed disulfide with cystine and is returned to the irrigation solution in is reduced form. With the aid of this cyclic action of 2-mercaptoethanol, the cells are able to utilize cystine constantly.

(5) A sodium bicarbonate buffer system is important in intracellular fluid to help maintain intercellular pH, fluid movement, corneal deturgesence, and membrane potential difference across mammalian cells, such as the corneal endothelium.

Various modifications can be made to the present invention without departing from the apparent scope thereof.

We claim:
1. An aqueous supplementary concentrate for addition to Balanced Salt Solution for Ringer's Solution to form a surgical solution, the concentrate consisting essentially of effective amounts of:
   a. water;
   b. a glycosaminogycan;
   c. an antioxidant;
   d. dextrose or a pyruvate, or both;
   e. an amino acid; and,
   f. a bicarbonate buffer.
2. The concentration of claim 1 wherein (b) is chondroitin sulfate, dermatan sulfate, haparan sulfate, heparin sulfate or hyaluorinic acid; (c) is 2-mercaptoethanol, ascorbic acid or glutathione; (d) is a pyruvate or dextrose; and (e) is cystine, inosine, adenine or adenosin.
3. The concentrate of claims 1 or 2 wherein the components are present in the following concentrations:
   (b) 0.001-550 mg/ml
   (c) 0.1-10 mM
   (d) 0.5-100 mM
   (e) 0.1-50 mM
   (f) 0.01-100 mM
4. A supplementary concentrate for addition to Balanced Salt Solution or Ringer's Solution to form a surgical solution, the concentrate consisting essentially of:
   a. water;
   b. chondroitin sulfate, 0.001-550 mg/ml;
   c. 2-mercaptoethanol, 0.1-10 mM;

d. a pyruvate, 0.5–100 mM;
e. cystine, 0.1–50 mM; and,
f. sodium bicarbonate, 0.01–100 mM 5. A concentrate according to any one of claims 1 and 4 additionally containing at least one cell growth factor or growth supplement.

6. The concentrate of claim 5 in which the factor or supplement is laminin, fibronectin, fibroblastic growth factor, endothelial cell growth supplement, urogastrone, epidermal growth factor, bovine pituitary extract, insulin, IV collagen, enactin, ethanolamine, phosphoethanolamine or sialic acid.

* * * * *

UNITED STATES PATENT AND TRADEMARK OFFICE
CERTIFICATE OF CORRECTION

PATENT NO. : 4,886,786
DATED : December 12, 1989
INVENTOR(S) : Richard L. Lindstrom; Debra L. Skelnik It is certified that error appears in the above—identified patent and that said Letters Patent is hereby corrected as shown below:

Column 1, line 54, change "a" to --as--.

Column 1, line 57, before "and" insert --stabilization--.

Column 3, line 39, delete "in"; and delete "14" and insert --(a dash "-")--.

Column 3, line 40, delete "Dl-y-tocopheral" and insert --dl-α-tocopheral--.

Column 8, line 42, delete "for" and insert --or--.

Column 8, line 53, delte "hyaluorinic" and insert --hyaluronic--.

Column 8, line 55, delte "adenosin" and insert --adenosine--.

Signed and Sealed this

Fifteenth Day of January, 1991

Attest:

HARRY F. MANBECK, JR.

*Attesting Officer*  *Commissioner of Patents and Trademarks*